(12) United States Patent
Sharma et al.

(10) Patent No.: US 6,891,050 B2
(45) Date of Patent: May 10, 2005

(54) PROCESS FOR THE PREPARATION OF TAXANES SUCH AS PACLITAXEL, DOCETAXEL AND STRUCTURALLY SIMILAR ANALOGS

(75) Inventors: Arun Prakash Sharma, Nadia (IN); Subrata Sarkar, Nadia (IN)

(73) Assignee: Dabur India Limited, Kalyani (IN)

( * ) Notice: Subject to any disclaimer, the term of this patent is extended or adjusted under 35 U.S.C. 154(b) by 96 days.

(21) Appl. No.: 10/213,431

(22) Filed: Aug. 7, 2002

(65) Prior Publication Data

US 2003/0045732 A1 Mar. 6, 2003

Related U.S. Application Data

(60) Provisional application No. 60/311,077, filed on Aug. 10, 2001.

(51) Int. Cl.[7] ............................................. C07D 305/14
(52) U.S. Cl. ........................................ 549/510; 549/511
(58) Field of Search ................................. 549/510, 511

(56) References Cited

U.S. PATENT DOCUMENTS

| | | |
|---|---|---|
| 5,476,954 A | 12/1995 | Bourzat et al. |
| 5,616,739 A | 4/1997 | Mas et al. |
| 5,637,723 A | 6/1997 | Commercon et al. |
| 6,002,022 A | 12/1999 | Authelin et al. |
| 6,022,985 A | 2/2000 | Authelin et al. |
| 6,197,980 B1 | 3/2001 | Durand et al. |
| 6,506,905 B1 | 1/2003 | Prakash et al. |

OTHER PUBLICATIONS

U.S. Appl. No. 10/431,499, Sharma et al., filed Aug. 5, 2003.

U.S. Appl. No. 10/430,433, Sharma et al., filed May 7, 2003.

U.S. Appl. No. 10/358,384, Sharma et al., filed Feb. 5, 2003.

U.S. Appl. No. 10/419,782, Sharma et al., Apr. 22, 2003.

U.S. Appl. No. 10/213,431, Sharma et al., Aug. 7, 2002.

Wani et al., J. Am. Chem. Soc., vol. 93, pps. 2325–2326 (1971).

*Primary Examiner*—Ba K. Trinh
(74) *Attorney, Agent, or Firm*—Marina V. Schneller; Venable LLP

(57) ABSTRACT

A process for the preparation of taxanes including paclitaxel, docetaxel, and structurally similar analogs, as well as intermediates produced by the process.

26 Claims, 1 Drawing Sheet

PROCESS FOR THE PREPARATION OF TAXANES SUCH AS PACLITAXEL, DOCETAXEL AND STRUCTURALLY SIMILAR ANALOGS

This application claims the benefit of Provisional Application No. 60/311,077, filed Aug. 10, 2001.

This invention relates to a process for the preparation of taxanes such as paclitaxel, docetaxel and structurally similar analogs.

FIELD OF THE INVENTION

This invention relates to a process for the preparation of taxanes such as paclitaxel, docetaxel and structurally similar analogs. The taxanes are very important anticancer drugs.

BACKGROUND OF THE INVENTION

Paclitaxel is an approved drug for refactory advanced ovarian cancer, breast cancer and most recently AIDS-related Kaposi's sarcoma. It is a diterpene taxane found in very low concentration in the bark of Pacific yew tree *Taxus brevifolia* but its biogenetic precursor, 10-deacetylbaccatin, 10-DAB 1 is found in relatively much higher concentration. Because of complex structure of taxane nucleus, total synthesis routes are very long and tedious and therefore appear uneconomical compared to semisynthesis.

Since, there is great interest in the semisynthesis of paclitaxel to meet its growing demand; 10-DAB has emerged as a key raw material for synthesis of paclitaxel, docetaxel and their analogs.

A synthetic protocol for the conversion of 10-DAB into taxoal requires a) selective acylation/protection at similarly reactive C-7 and C-10 hydroxyl groups. Among the 1,7,10 and 13-hydroxyl groups present in the 10-DAB, the order of reactivity is 7>10>13>1. Therefore, selective esterification of 13-hydroxyl requires protection of both 7 and 10-hydroxyl. If acetyl group at C-10 is required, as in the synthesis of paclitaxel, then 7-hydroxyl is to be protected first followed by acetylation at 10-hydroxyl.

b) selective esterification of C-13 hydroxyl group with a suitably protected N-benzoylphenylisoserine. It has been found that α-hydroxy-β-amidoacyl moiety at 13-hydroxyl of taxane is very essential for anticancer activity (Wani et al J.Am.Chem. Soc. 93, pp2325, 1971). Esterification at 13-hydroxyl is very sluggish due to its stereo-electronic disposition. Hence, the apparently simple reaction has become a very important step in assembling of the side chain and 13-hydroxytaxane. It is known from the literature that with cyclic forms of α-hydroxy-β-amidoalkylcarboxylic acid, the side chain precursors, esterification step proceeds to completion in high yield. Therefore, new cyclic forms of side chains, which give high yield of coupled product under simple reaction conditions without their use in large excess, are required to develop new semi-synthetic routes for paclitaxel and its analogs.

c) conversion of side chain precursor part into side chain and removal of protecting groups from baccatin part. These reaction conditions should be mild in nature affording the final material in high yield with very few side products. For successful commercial production, it is very much desired that the crude semi-synthetic taxane anticancer molecules should be produced with such purity that they could easily purified into pharmaceutical grade material. Because of very sensitive nature of taxane nucleus, it is highly prone to degradation and the desired semi-synthetic crude materials are often produced contaminated with structurally similar impurities, very difficult to separate completely.

Thus, it is obvious that new 13-hydroxytaxanes (more specifically 13-hydroxy-7,10-dihydroxyprotected-10-deacetylbaccatin and 13-hydroxy-7-hydroxyprotected baccatin) and the novel side chain precursors are sought for development of more facile routes of semisynthesis of taxane anticancer drugs.

As mentioned above, for esterification at 13-hydroxy, 7 and 10-hydroxy need to be protected/derivatised first. With this in view, we started exploring use of haloalkyl acid chlorides 2 as protecting groups for both 7 and 10 hydroxy. These protecting groups undergo hydrolysis faster than unsubstituted alkyl acid chlorides. Therefore, it is possible to deprotect these groups without many side products in presence of acetyl group under same condition. We have actually found that haloalkyl acid chlorides such as 1-halo/2,2-dihaloacyl chlorides can be used for selective protection and deprotection in taxane. Thus we have found 7-O-(2-haloacyl)baccatin and 7,10-O-di-(2-haloacyl)-10-DAB and similar haloacyl protected-taxanes as new types of intermediates for synthesis of taxanoid anticancer drugs, more specifically paclitaxel and docetaxel.

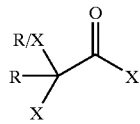

2

In order to develop such side chain precursor which can produce paclitaxel/docetaxel after joining with taxane under very mild and preferably neutral condition, it was found that oxazolidine carboxylic acid 3 is a suitable side chain precursor. These side chain precursors have (alk-2-ynyloxy) carbonyl group as nitrogen protecting group. This group is cleaved under neutral conditions; therefore degradation of taxane can be avoided. The other N,O-bifunctional protecting group then undergoes cleavage very fast without any degradation under very mild condition. Most of the nitrogen protecting groups used so far either require harsh acidic conditions or hydrogenolysis for their removal. Therefore, these 3-(alk-2-ynyloxy) oxazolidines have emerged as new type of side chain precursors.

Herein we have described new intermediates for taxanoid anticancer drugs, their process of synthesis and process for synthesis of paclitaxel and similar analogs using them in (Scheme-1).

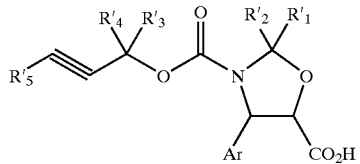

3

OBJECTS OF THE INVENTION

An object of this invention is to propose a new process for the preparation of taxanes.

Another object of this invention is to propose a process for the preparation of novel intermediates of taxanes.

Yet another object of this invention is to propose a process of preparing paclitaxel using the intermediates which help in minimizing degradation of products and also increase the purity of the end product.

Yet another object of this invention is to propose a process for selective protection of 7-hydroxyl and 7,10-hydroxyls of 1,7,10,13-tetrahydroxy taxanes with 2-halo acyl groups.

Still another object of this invention is to propose a new process for the production of baccatin III and 10-hydroxyl protected-10-deacetyl baccatin-III which are useful intermediates in the synthesis of taxanes.

SUMMARY OF THE INVENTION

The present invention relates to a process for the preparation of taxanes comprising:

suspending 10-DAB of general structure 1 in a haloalkane and treating the suspension with haloalkyl acid chloride/dihaloakyl acid chloride in the presence of an activating agent and an organic base at temperature between −20 to 40° C. to obtain 7-O-haloacyl taxane 2'a along with a minor amount of 7,10-dihaloacyl taxane 2'b;

treating 7-O-(2-haloacetyl)trihydroxytaxane 2'a with acetyl chloride/acetic anhydride in the presence of an amine and a solvent at −20 to +40° C. to obtain 7-O-(2-haloacyl)-10-acetyldihydroxy taxane 2'c;

subjecting acetyldihydroxy taxane 2'c to the step of deprotection under mild alkaline condition at −20 to +40° C. in the presence of ammonia/aliphatic amine/aromatic amine or their combination to remove the 2-haloacetyl group without degradation to produce baccatin III;

subjecting 7,10-diprotected intermediates, 7-O-(2-haloacyl)-10-acetyldihydroxy taxane 2'c or 7,10-di-(2-haloacyl)dihydroxytaxane 2'b to the step of coupling with 3-(alk-2-ynyloxy)carbonyl-5-oxazolidine carboxylic acid of general structure 3 in the presence of a condensation agent and an activating agent and ether to obtain 7-O-[2-(haloacyl)]-10-acetyl-13-[(alk-2-ynyloxy)carbonyl-5-oxazolidinecarboxyl] monohydroxytaxane 4a (from 2'c) and 7,10-di[2-(haloacyl]-13-[(alk-2-ynyloxy)carbonyl-5-oxazolidinecarboxyl]monohydroxytaxane 4b;

reacting the coupled products 4a & 4b with an acid to open the oxazolidine ring by removal of the alk-2-ynyloxycarbonyl protecting group to obtain the free amines of structure 5;

treating the free amine of structure 5 with acid chlorides or acid anhydrides in the presence of a base in a heterogenous phase to obtain the intermediate 6;

subjecting the intermediate 6 to the step of deprotection of 2-haloacyl/2,2-dihaloacyl groups without degradation to obtain paclitaxel or docetaxel under mild condition at −20 to +40° C. for 6–24 h in the presence of ammonia or aliphatic amines or aromatic amines or their combination.

The complete reaction scheme is shown in the reaction scheme, set forth in FIG. I.

DETAILED DESCRIPTION OF THE INVENTION

Figure 1:
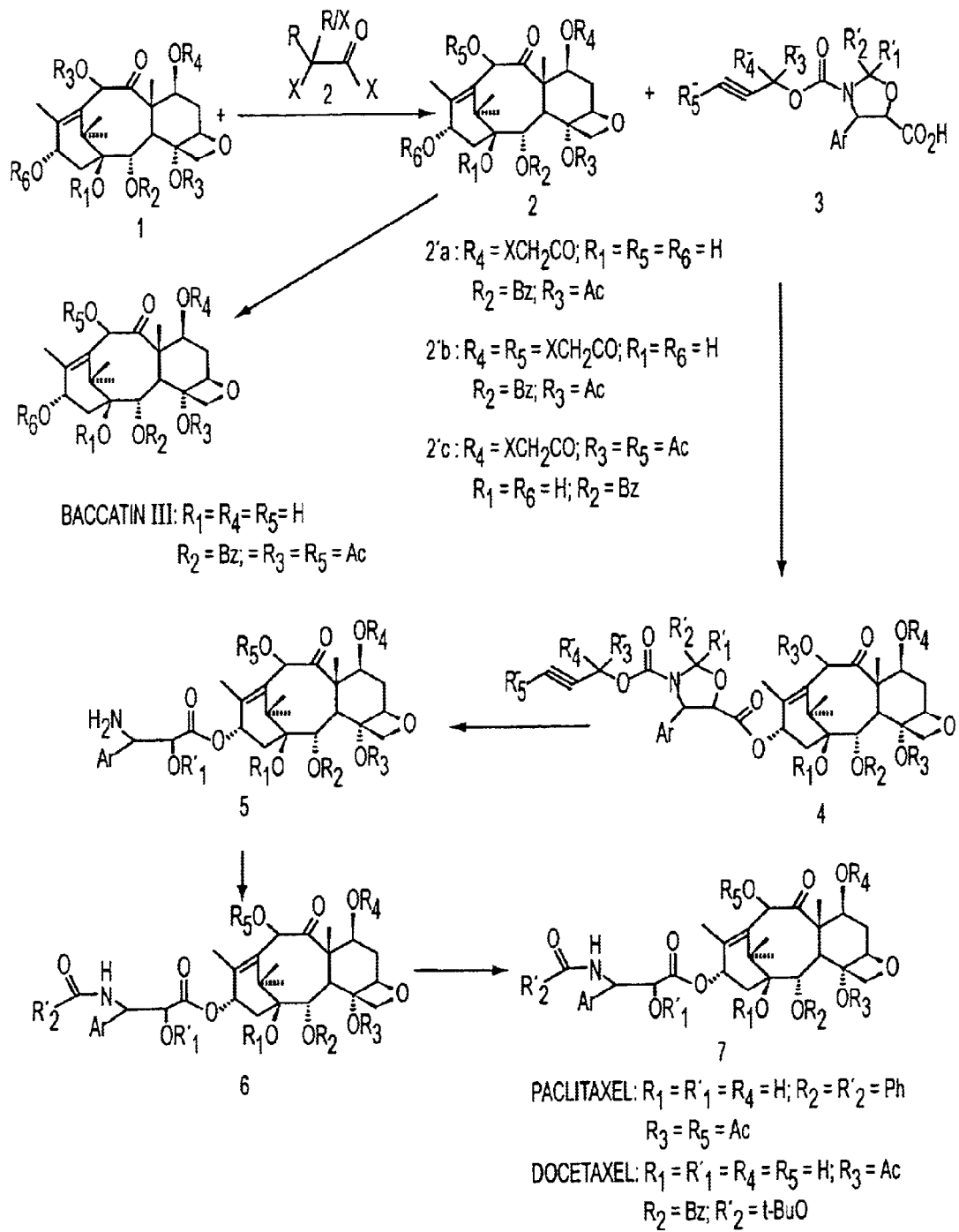
FIG. 1 is the reaction scheme of the process of the invention. It reveals that 10-DAB can produce any one of three ultimate products including BACCATIN III; Paclitaxel and Docetaxel.

The present invention provides a process for the preparation of taxanes and its analogs. 10-DAB of general structure 1 is suspended in a haloalkane and the suspension is treated with haloalkyl acid chloride/dihaloalkyl acid chloride in the presence of an activating agent and an organic base at temperature between −20 to 40° C. to obtain 7-O-haloacyl taxane 2'a along with a minor amount of 7,10-dihaloacyl taxane 2'b.

The activating agent used can be an aromatic amine, preferably an aminopyridine or dialkylaminopyridine, most preferably 4-dimethylaminopyridine. Among organic bases used nitrogenous bases are preferable, more preferably an aromatic nitrogenous base e.g. pyridine is found to be most suitable.

7-O-(2-haloacetyl)trihydroxytaxane 2'a is treated with acetyl chloride/acetic anhydride in the presence of an amine and a solvent at −20 to +40° C. to obtain 7-O-(2-haloacyl)-10-acetyldihydroxytaxane 2'c.

The preferred amines are aromatic amines, more preferably it is pyridine, which can act as base as well as solvent.

Further, formation of 7,10-dihaloacyl taxane 2'b is minimized by carrying out the reaction by slow addition of a dilute solution of 1.4 to 1.8 equivalents, preferably 1.55 equivalents of haloalkyl acid chloride in a haloalkane into a suspension of 10-DAB in the same haloalkane in the presence of 2 equivalents of organic base and catalytic amount of activating agent. The crude obtained thus is dissolved in an aliphatic nitrile. Preferably acctronitrile at 60–80° C. cooling the resultant solution to room temperature and then filtering it. The filtrate is evaporated to obtain 7-O-haloacyl taxane 2'a.

In the synthesis of docetaxel it is desirable to protect both 7 and 10-hydroxyl groups of taxanes with protecting groups which can be deprotected under mild reaction condition later on, after the 7,10-diprotected taxane has been coupled with a suitable side chain at the 13-position. Under the present investigation it is found that both 7 and 10-hydroxyl groups of taxanes can be protected with haloacyl or dihaloacyl groups under similar condition as described above by using 2.5–3.0 equivalents of the corresponding acid chlorides to obtain taxane intermediate 2'b.

In the present invention any straight chain or branched haloalkane having up to 10 carbon atoms can be used as solvent. The preferable haloalkane is chloroalkane. More specifically dichloromethane can be used as solvent. The haloalkyl acid chloride used in the process is preferably a 2-haloalkyl acid chloride or a 2,2-dihaloalkyl acid chloride.

Among 2-haloalkyl acid chlorides, 2-chloroacetyl chloride is preferable while 2,2-dichloroacetyl chloride is found to be most suitable among 2,2-dihaloalkyl acid chlorides. Chloroalkyl acid chlorides were preferred than the corresponding bromo or fluoroalkyl acid chloride as they are cheaper and more easily available.

Acetyldihyroxytaxane 2'c is subjected to the step of deprotection under mild alkaline condition at −20 to +40° C. in the presence of ammonia/aliphatic amine/aromatic amine or their combination to remove the 2-haloacetyl group without degradation to produce baccatin III. Baccatin III is precursor of a number of pharmacologically active taxanoids.

7,10-diprotected intermediates, 7-O-(2-haloacyl)-10-acetyldihydroxy taxane 2'c or 7,10-di-(2-haloacyl) dihydroxytaxane 2'b is subjected to the step of coupling with 3-(alk-2-ynyloxy)carbonyl-5-oxazolidine carboxylic acid of general structure 3 in the presence of a condensation agent and an activating agent and ether to obtain 7-O-[2-(haloacyl)]-10-acetyl-13-[(alk-2-ynyloxy)carbonyl-5-oxazolidinecarboxyl] monohydroxytaxane 4a (from 2'c) and 7,10-di[2-(haloacyl]-13-[(alk-2-ynyloxy)carbonyl-5-oxazolidinecarboxyl]monohydroxytaxane 4b.

The reaction is carried out at temperature between 0°-60° C., more preferably at 25–65° C., most preferably at 60° C. Among ethers tetrahydrofuran is found to be most suitable. The coupled products 4a & 4b are reacted with an acid to open the oxazolidine ring by removal of the alk-2-ynyloxycarbonyl protecting group to obtain the free amines of structure 5.

The opening of oxazolidine ring is effected by acids via formation of an alkyne-Co complex by virtue of its strong stabilisation of a cationic charge at its α-position. A solution of intermediate 4a/4b in TFA in chloroalkane, preferably dichloromethane is stirred with 1–1.5 equivalents cobalt carbonyl at 20–40° C., most preferably at 25° C. for ½ to 2 h, prefer obtain the free amines 5.

The free amine of structure 5 is treated with acid chlorides or acid anhydrides in the presence of a base in a heterogenous phase to obtain the intermediate 6.

The intermediate 6, under mild alkaline condition preferably at 0° C., for 6–24 h, more preferably 12 h, in the presence of ammonia or aliphatic amines or aromatic amines or their combination, preferably ammonia and pyridine, more preferably a mixture of 1:10 ammonia and pyridine undergoes selective deprotection of 2-haloacyl/2,2-dihaloacyl groups without degradation to afford Paclitaxel or Docetaxel.

3-(Alk-2-ynyloxy)carbonyl-5-oxazolidine carboxylic acid 3 is obtained by condensing arylisoserine, with alk-2-ynylhaloformate in the presence of a base to obtain N-(alk-2-ynyloxy)carbonylisoserine which is then converted to the corresponding methyl ester and the said ester is treated with an alkoxyalkane in the presence of catalytic amount of arylsulfonic acids to obtain 3-(alk-2-ynyloxy)carbonyl-5-oxazolidine carboxylic esters, which on alkaline hydrolysis provide the desired compound 3.

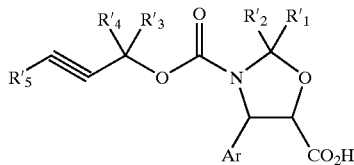

3

R'1 and R'2 are independently selected from hydrogen, alkyl, alkenyl, alkynyl, aryl, heteroaryl, alkoxy, alkenoxy, alkynyloxy, aryloxy, and heteroaryloxy. In the preferred structure R'1 is hydrogen and R'2 is aryl, more preferably p-methoxybenzene.

R'3 and R'4 are independently selected from hydrogen, alkyl, alkenyl, alkynyl, aryl and heteroaryl. In the preferred structure both R'3 and R'4 are hydrogen.

R'5 is hydrogen, aryl, heteroaryl, alkyl, alkenyl, and alkynyl. The preferred substitution is aryl. The aromatic moiety itself could be substituted or unsubstituted. The more preferred substitution is o,m,p-anisyl, among which p-anisyl is the most preferred.

Experiment-1: 7-O-(2-Chloroacetyl)-10-deacetylbaccatin

10-Deacetylbaccatin (109 gm, 0.2 mol) is suspended in dichloromethane (1.1 L). 4-Dimethylamino pyridine (1.0 gm, 0.008 mol) is then added & the mixture is stirred at room temperature for 15 min. To this stirred mixture a solution of chloroacetyl chloride (35 gm, 0.31 mol) in dichloromethane (2.0 L) is added dropwise. Stirring is then continued for 25–30 min to obtain a clean solution. The reaction is monitored by TLC. It is quenched by slow addition of water (100 ml) to the reaction mixture. 10% Dil. hydrochloric acid is then added to bring the pH 3–3.5 and the layers are separated. The organic layer is washed with water (3×200 ml) followed by brine (3×200 ml) and then evaporated to obtain crude 7-O-chloroacetyl-10-deacetylbaccatin. The crude was suspended in acetonitrile (1.15 L) and dissolved at 75° C. The solution is cooled to room temperature and then kept under stirring for 15 min. The precipitated 10-DAB is filtered out. The filtrate is evaporated to obtained the title compound (115 gm).

Experiment-2: 7,10-[Di-O-(2-chloroacetyl)10-deacetylbaccatin 7,10-O-Dichloroacetyl-10-deacetylbaccatin is obtained by using 3.0 equivalent of chloroacetylchloride and following the protocol described in Experiment-1.

Experiment-3: 7-O-(2-Chloroacetyl)baccatin

7-O-Chloroacetyl-10-deacetylbaccatin (115 gm, 0.185 mol) is dissolved in pyridine (1.15 L) at room temperature under nitrogen. The solution is cooled to 0–5° C. and then acetic anhydride (150 ml) is added dropwise. Stirring is continued for 24 h when TLC indicated completion of the reaction. Water (200 ml) is then added to reaction mixture slowly under stirring. Pyridine is evaporated under vacuum at 40° C.

The resulting gum is dissolved in dichloromethane (500 ml) and pH of the solution is brought to 3–3.5 by using 10% dilute hydrochloric acid. The organic layer is then separated and washed successively with water (3×100 ml) and brine (3×100 ml). Evaporation of the organic layer provides 7-O-(2-chloroacetyl)baccatin (115 gm).

Experiment-4: Baccatin III

7-O-(2-Chloroacetyl)baccatin (110 gm, 0.165 mol) is dissolved in pyridine (1.1 L) under nitrogen at room temperature, cooled to 0° C. and then 25% aq ammonia solution (220 ml) is added. Stirring is continued at 0° C. for 8 h and then ammonia is removed by bubbling nitrogen through the reaction mixture. Pyridine is removed under vacuum at 40° C. The resulting gum is dissolved in dichloromethane and then 10% hydrochloric acid is added to bring the pH to 3.5–4. The organic layer is separated and then successively washed with water (3×100 ml) and brine (3×100 ml). Evaporation of organic layer, thus obtained, under reduced pressure provided baccatin III.

Experiment-5: 7-O-[2-(Chloroacetyl)-13-[(prop-2-ynyloxy) carbonyl-5-oxazolidine]carboxyl baccatin III 4a A mixture of 7-O-[2-(chloroacetyl)]baccatin III (2'c, 100 gm, 0.15 mol), 3-(prop-2-ynyloxy)carbonyl-5-oxazolidine carboxylic acid(3, 100 gm, 0.26 mol) and 4-dimethylaminopyridine (10 gm, 0.082 mol) is dissolved in THF (1.0 L) under nitrogen atmosphere. The internal temperature is raised to 50° C. under stirring and then a solution of DCC(80 gm) in THF(200 ml) is added to it. Temperature of the reaction mixture automatically rises to 65° C. and is maintained for about 30 min. The reaction mixture is cooled to room temperature, diluted with ethyl acetate(8.0 L) and kept under stirring for 15 min. It is then filtered under suction. The residue is extracted with ethyl acetate(2×2.0 L) and the extracts are added to the filtrate obtained above. The combined organic layer is washed successively with 25% ammonium chloride solution(2×2.0 L), 5% aq. sodium bicarbonate (2×2.0 L), water (2×2.0 L), brine (2×2.0 L), and then dried over anh. sodium sulfate for 1 h. Evaporation of the organic layer under reduced pressure provided the crude product, which is then precipitated with DCM/hexane (1:10) to obtain the title compound 4a (125 gm).

Experiment 6: 7-O-[2-(Chloroacetyl)]paclitaxel 6

To a precooled solution (0–5° C.) of TFA in dichloromethane (1.25 L) 7-O-[2-(Chloroacetyl)-13-[(prop-2-ynyloxy)carbonyl-5-oxazolidine]carboxyl baccatin III 4a (125 gm, 0.122 mol)) is added followed by dicobalt octacarbonyl (50 gm, 0.146 mol) under stirring. Stirring is continued for 3 h and then 5% aq. sodium bicarbonate is added. The reaction mixture is cooled and a solution of benzoyl chloride (26.5 gm, 0.19 mol) in dichloromethane (265 ml) is added under stirring at 0–5° C. After the addition is over, stirring is continued for 15 min. The organic layer is then separated, washed with brine and stored over sodium sulfate for 1 h. Evaporation of the organic layer under reduced pressure yield the title compound.

Experiment 7: Paclitaxel

To a precooled solution (0–5° C.) of 25% ammonia (35 ml) in pyridine (350 ml) is added 7-O-[2-(chloroacetyl)] paclitaxel (35 gm, 37.65 mmol) and then stirred at this temperature for 8 h. The reaction is monitored by TLC. After the reaction is over ammonia is removed by bubbling nitrogen through the reaction mixture at 0–5° C. and then pyridine is removed under low pressure at 15–20° C. The resultant gum is dissolved in ethyl acetate(500 ml). The organic layer is washed successively with 2% hydrochloric acid, 5% sodium bicarbonate, brine and stored over anh. sodium sulfate. The organic layer is evaporated under reduced pressure to obtain paclitaxel (30 gm, 35.17 mmol).

We claim:

1. A process for the preparation of intermediates 2' comprising:
   a) suspending 10-DAB in a haloalkane and then treating the suspension with a haloalkyl acid chloride or a dihaloalkyl acid chloride in the presence of an activating agent and an organic base at temperature between –20–40° C. to obtain 7-O-haloacyl taxane 2'a along with minor amount of 7,10-dihaloacyl taxane 2'b;
   b) treating 7-O-(2-haloacyl)trihydroxyl taxane ie 2'a thus obtained with acetyl chloride or acetic anhydride in the presence of an amine and a solvent at –20 to +4° C. to obtain 7-O-(2-haloacyl)-10-acetyl-dihydroxy taxanes 2'c.

2. A process as claimed in claim 1, wherein said activating agent is an aromatic amine; preferably an aminopyridine or dialkylaminopyridine.

3. A process as claimed in claim 1, wherein said organic base used are nitrogenous bases, preferably an aromatic nitrogenous base such as pyridine.

4. A process as claimed in claim 1, wherein formation of 2'b can be minimized by carrying out the reaction by slow addition of a dilute solution of 1.4 to 1.8 equivalents of haloalkyl acid chloride in a haloalkane into a suspension of 10-DAB in the presence of 2 equivalents of organic base and catalytic amount of activating agent. The crude obtained thus is dissolved in an aliphatic nitrile at 60–80° C., cooling the resultant solution to room temperature and then filtering it, the said filtrate is evaporated to obtain only 7-O-haloacyl taxane 2'a.

5. The intermediates of formula 2'a, 2'b and 2'c.

6. A process for the preparation of baccatin III comprising:
   suspending 10-DAB of general structure 1 is suspended in a halo alkane & treating the suspension with haloalkyl acid chioride/dihaloalkyl acid chloride in the presence of an activating agent and an organic base at temperature between –20 to 40° C. to obtain 7-O-haloacyl taxane 2'a along with minor amount of 7,1 0-dihaloacyl taxane 2'b;
   treating 7-O-(2-haloacyl)trihydroxytaxane 2a with acetyl chloride/acetic anhydride in the presence of an amine and a solvent at –20 to +4° C. to obtain 7-(2-haloacyl)-10-acetyl-dihydroxy taxanes 2'c;
   subjecting acetyldihydroxytaxane 2'c the step of deprotection under mild alkaline condition at –20 to +4° C. in the presence of ammonia or aliphatic amine/aromatic amine or their combination to remove the 2-haloacetyl group without degradation to produce baccatin III.

7. A process as claimed in claim 6, wherein the said amines are aromatic amities preferably pyridine in combination with aqueous ammonia.

8. A process for the preparation of at least one taxane selected from the group consisting of as Paclitaxel and Docetaxel
   a) suspending 10-DAB of general structure 1 in haloalkane and treating the suspension with 2-haloalkyl acid chloride in presence of an activated agent and an organic base to obtain 7-O-haloacyl taxane (2'a), or 7,10-O-dihaloacyl taxane (2'b), or admixtures of (2'a) and (2'b);
   b) treating 7-O-(2-haloacetyl) taxane (2'a) with acetyl chloride or anhydride in the presence of an amine and solvent to obtain 7-O-(2-haloacetyl)-10-acetyl taxane (2'c);
   c) coupling either 7-O-(2-haloacetyl)-10-acetyl taxane (2'c) or 7, 10-dihaloacyl taxane (2'b) with 3-(alk-2-ynyloxy)carbonyl-5-oxazolidine carboxylic acid of general structure 3 in the presence of a condensing agent and an activating agent in ether to obtain7-O-(2-haloacetyl)-10-acetyl-13[(alk-2-ynyloxy)carbonyl-5-oxazolidine carboxyl] taxane 4a (from 2'c) and 7,10-di(2-haloacyl)-13-[(alk-2-ynyloxy)carbonyl-5-oxazolidine carboxy] taxane 4b (from 2'b);
   d) reacting the coupled product 4a or 4b with acid and dicobalt octacarbonyl to open the oxazolidine ring to obtain a free amine intermediate of 4a or a free amine intermediate of 4b, respectively;
   e) treating either of the free amine intermediates with acid chloride or anhydride in presence of a base in heterogeneous phase to obtain an intermediate 6;
   c) subjecting the intermediate 6 by deprotection of 2-haloaceyl under mild alkaline condition to obtain Paclitaxel or Docetaxet.

9. A process as claimed in claim 8, wherein said haloalkane, in 1(a) is dichioromethane.

10. A process as claimed in claim 8, wherein said 2-haloalkyl acid chloride in 1(a) is 2-chloroacetyl chloride and wherein dihaloalkyl acid chloride is 2,2-dichloroacetyl chloride.

11. A process as claimed in claim 8, wherein said activated agent, in 1(a), is aminopyridine or dialkyl amino pyridine.

12. A process as claimed in claim 8, wherein said organic base, in 1(a), is pyridine.

13. A process claimed in claim 8, wherein, in 1(b) said amine is pyridine and solvent is dichioromethane.

14. A process claimed in claim 8, wherein the condensing agent in 1(c) is dicyclocarbodimide and the activating agent is 4-dimethyl aminopyridine.

15. A process claimed in claim 8 wherein the reaction, in 1(c), is carried out at 0–80° C.

16. A process claimed in claim 8 wherein the ether, in 1(c), is tetrahydrofuran.

17. A process claimed in claim 8 wherein the reaction in 1(d) is effected with acids by the formation of an alkyne-Co-complex by virtue of its strong stabilization of a cationic charge at its position.

18. A process claimed in claim 8, wherein the reaction, in 1(d), comprises reacting intermediate 4a/4b in chioroalkane with 1 to 1.5 equivalents cobalt carbonyl by stirring at 20–40° C. to obtain free amines designated 5a and/or 5b respectively.

19. A process as claimed in claim 8, wherein the said base is sodium bicarbonate.

20. A process claimed in claim 8, wherein the said acid chloride or anhydride, in 1(e) is benzoyi chloride for Paclitaxel and t-BOC anhydride for Docetaxel.

21. A process claimed in claim 8, wherein the said heterogeneous phase in 1(e) is Ethyl acetate-Aqueous sodium bicarbonate or Tetrahydrofuran-Solid sodium bicarbonate system.

22. A process claimed in claim 8, wherein the reaction temperature, in 1(e), is 0–25° C.

23. A process claimed in claim 8, wherein the said deprotection in 1(f) is done under mild alkaline condition at −20 to +40° C. in the presence of an aromatic amine.

24. A process claimed in claim 23, wherein the said aromatic amine is pyridine.

25. A process claimed in claim 8, wherein the said alkaline condition is effected by using ammonia.

26. A process for preparation of Baccatin III by deprotection of 2'c with ammonia-pyridine at 0–5° C.

* * * * *